United States Patent [19]

Peeler

[11] 4,130,114
[45] Dec. 19, 1978

[54] FLUID PRESSURE MEASURING OR TESTING SYSTEM AND BLEED REGULATOR VALVE THEREFOR

[75] Inventor: Donald H. Peeler, Hendersonville, N.C.

[73] Assignee: Sybron Corporation, Rochester, N.Y.

[21] Appl. No.: 764,341

[22] Filed: Jan. 31, 1977

[51] Int. Cl.² ............................................. A61B 5/02
[52] U.S. Cl. ............................. 128/2.05 G; 128/274; 73/748; 137/513.5
[58] Field of Search ............... 128/2.05 G, 2.05 A, 128/2.05 C, 2.05 M, 274; 137/513.5; 73/402

[56] References Cited

U.S. PATENT DOCUMENTS

| | | | |
|---|---|---|---|
| 3,254,671 | 6/1966 | Berliner | 128/2.05 G X |
| 3,893,478 | 7/1975 | Peters | 128/2.05 G X |
| 3,901,272 | 8/1975 | Banners et al. | 137/513.5 |
| 4,037,587 | 7/1977 | Kaneda et al. | 128/2.05 G |

*Primary Examiner*—Lee S. Cohen
*Attorney, Agent, or Firm*—Theodore B. Roessel; Joseph C. MacKenzie

[57] ABSTRACT

A sphygmomanometric system having a cuff, etc., and regulator valve for bleeding air out of the sphygmomanometer cuff so that the cuff pressure drops at a substantially constant rate. The valve is in the form of a closed rubber tube having a slit with a pin holding the slit slightly open. Air can therefore be freely pumped into the tube, out the slit and into the cuff, but cannot flow back except at a restricted rate.

22 Claims, 16 Drawing Figures

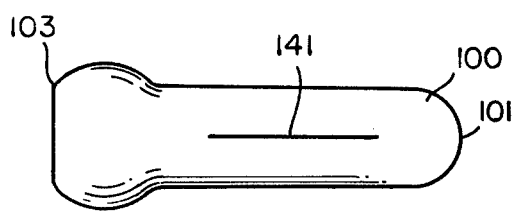
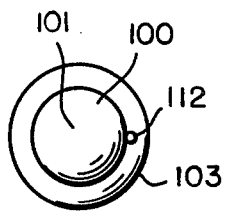
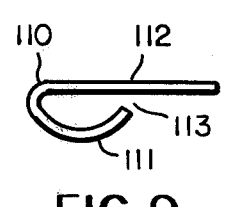
FIG. 7   FIG. 8   FIG. 9
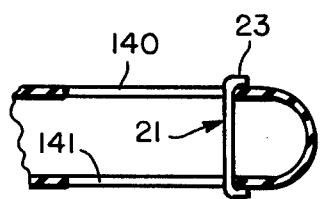
FIG. 11
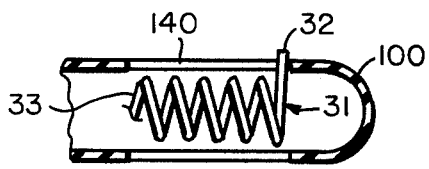
FIG. 10
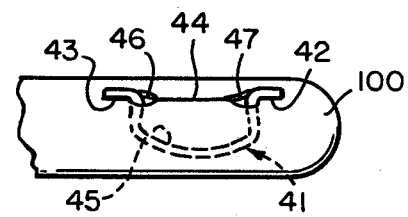
FIG. 13
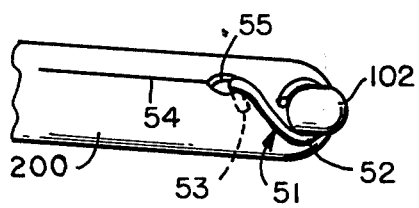
FIG. 12
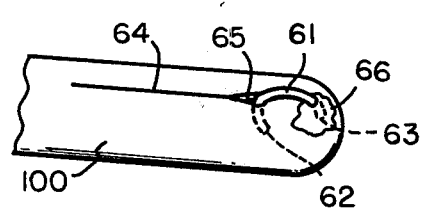
FIG. 14   FIG. 15
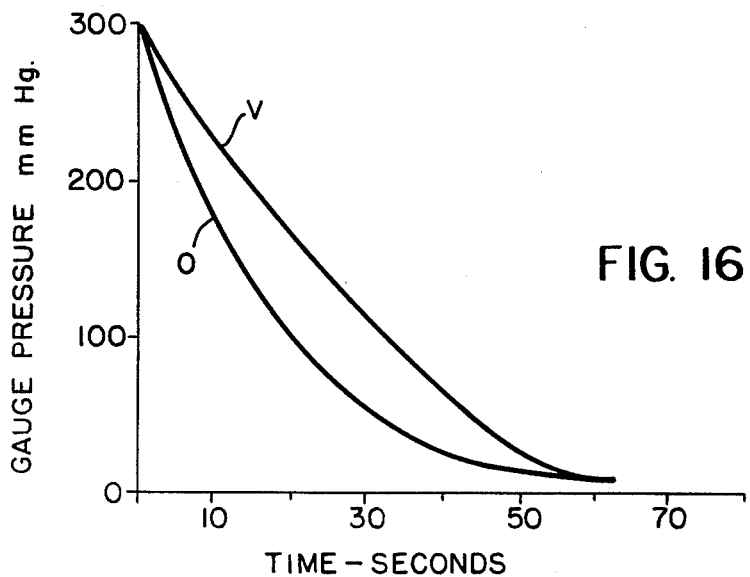
FIG. 16

4,130,114

FLUID PRESSURE MEASURING OR TESTING SYSTEM AND BLEED REGULATOR VALVE THEREFOR

FIELD OF THE INVENTION

The invention relates to measuring or testing with fluid pressure, especially sphygmomanometric systems wherein a cuff is first pumped up with air to occlude an artery, and then the air is allowed to bleed out of the cuff at a controlled rate, while the pressure in the cuff and sounds in the artery are being monitored. The invention also relates to regulator valves for bleeding air out of the cuff at a substantially constant rate of pressure change appropriate both for the subject whose blood pressure is being measured and for the person (who in some cases may be the subject) carrying out the measurement.

THE PRIOR ART

Such sphygmomanometric systems are well-known. However, the usual valve for bleeding the cuff is some sort of manually-operable fluid restrictor. While some automatically-acting regulator valves have been proposed, they do not seem to have been successful adjuncts to manually-operated forms of sphygmomanometer systems, and, in the past have mostly been found in more or less expensive automated sphygmomanometer systems.

One object of the present invention is to provide a new and improved fluid pressure testing system comprising fluid-containing means and a regulator valve for bleeding fluid from said means. It is also an object of the invention to provide a new and improved form of regulator valve for bleeding fluid from a fluid-containing means. Finally, it is particularly the object of the invention to provide a novel sphygmomanometric system using such regulator valve, and, as well, to provide, various species of such regulator valve.

SUMMARY OF THE INVENTION

The present invention in sphygmomanometric systems is characterized by fluid-containing means, such as a cuff, and a regulator valve for bleeding fluid, such as air in said cuff, from said fluid containing means, which regulator valve comprises a flexible tube which opens at a slit or slits therein, the edges of which are normally in sealing contact, except for a pin, which opens one slit slightly. Air in the tube can be forced freely out through said slit or slits, but cannot flow into said tube through said slit readily. The tube may have various forms, one being flat at one end, whereby the slit is formed between opposite sides of the tube end, but another being a tubular nipple with a slit or slits cut in it, there being a pin in one said slit, said pin being provided by a piece of wire, which is straight, curved, coiled, etc., depending on the mode of securing them in place.

BRIEF DESCRIPTION OF THE DRAWING

FIGS. 11 through 15 are fragmentary perspective views of other forms of regulator valve according to the invention.

FIG. 16 shows a pair of bleed curves, one being for a fixed orifice and the others being for a regulator valve according to the invention.

DESCRIPTION OF THE PREFERRED EMBODIMENTS

Figure 1:
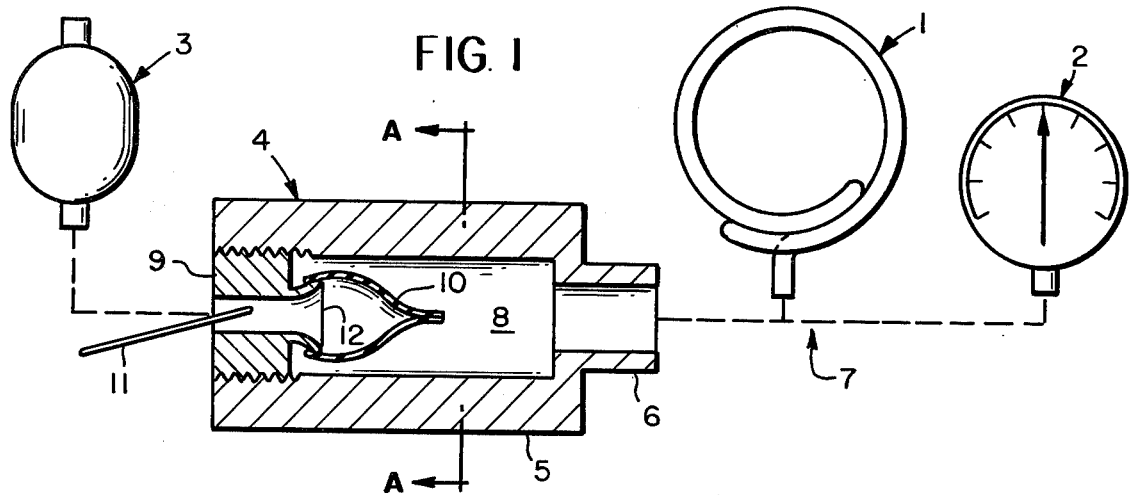
FIG. 1 is a schematic diagram of a sphygmomanometric system according to the invention, including one form of regulator valve in accordance with my invention, FIGS. 2 and 3 being sectional views of details of the regulator valve.

In FIG. 1, the sphygmomanometer system according to the invention includes the usual cuff 1, pressure gauge 2, and bulb 3, and as well, one form of my novel regulator valve 4,.

Valve 4 comprises a housing 5 having a fitting 6 for connection to cuff 1 and gauge 2 via tubing 7 or like fluid connector means. Fitting 6 opens into one end of a chamber 8 in casing 5, and said chamber terminates at its other end at a fitting 9. A flexible-walled tube 10 and pin 11 provide the active part of the valve 4, tube or nipple 10 being of rubber or the like, and having one end stretched over flared portion 12 of fitting 9, with pin 11 being shown as partly received in the bore of fitting 9.

Figure 2:
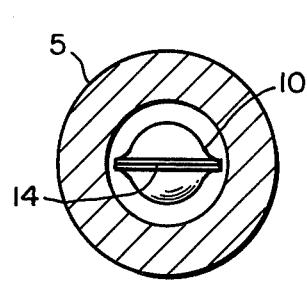

As will be seen from FIG. 2, which is a view on the plane A-A of FIG. 1, sectioning casing 5, the end of tube 10, distal from flared portion 12 is flat, so as to form a slit 14 by the contact between the opposed interior surfaces of the flattened walls of the tube. Supposing the flat end of tube to have been formed that way (or provided with suitable spring means, not shown, which force it into in a flat state), it will be evident that if the fluid pressure in chamber 8 is higher than inside tube 10, it will hold the tube end in the flat state shown in FIG. 2. However, it will be equally evident that if the fluid pressure in chamber 8 is enough less than the pressure inside nipple 10, then fluid will be forced through the slit 14 into chamber 8.

Thus, if bulb 3 be connected by suitable connector means (e.g. tubing not shown) to the bore of fitting 9 and operated in the manner usual in sphygmomanometry, air will be forced through tube 10 into chamber 8, and thence, via fitting 6 and tubing 7 into cuff 1 and gauge 2. Further, when the pumping ceases, the pressure in chamber 8, which will be higher than the pressure of the atmosphere from whence bulb 3 draws the air, and in which the whole apparatus is immersed, will cause the slit 14 to tightly seal.

Of course, in sphygmomanometry, such pressurization of the cuff is carried out to the point of totally occluding blood flow through an artery of a limb encircled by the cuff, and then allowed to bleed off at an appropriate rate.

Figure 3:
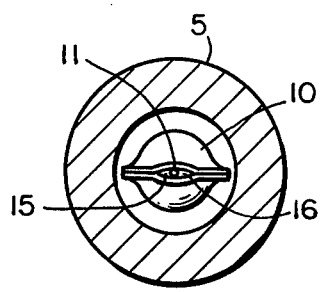

In the present case, such appropriate rate is provided for by inserting the pin 11 into the tube 10 until it opens the slit 14 as shown at 15 and 16 in FIG. 3. This has the interesting and useful result that the bleed through openings 15 and 16, to atmosphere, provides a substantially constant rate of pressure drop from 250–300 mm Hg above atmosphere, to around 25 mm Hg above atmosphere, because as the pressure in chamber 8 approaches atmosphere the openings 15 and 16 increase. This is due to the fact that the force trying to close the slit acts less and less strongly as the pressure in chamber 8 decreases due to air bleeding through openings 15 and 16 to atmosphere.

Such regulation of bleed is not obtainable with a fixed orifice, as will be seen from FIG. 16, which shows a fixed orifice bleed curve O between the same pressure values and over the same time as the curve V which shows the performances of my novel regulator valve. In short, with a bit of wire and rubber tubing, I provide a regulator valve giving a constant rate of cuff pressure decrease which is ideal for sphygmomanometry.

Figure 4:
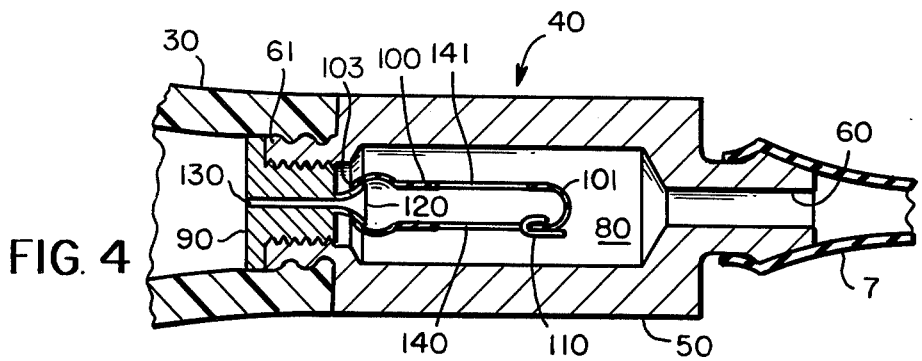
FIG. 4 is a sectional elevation of a preferred form of regulator valve according to the invention, FIGS. 5 through 10 showing various details of the FIG. 4 regulator valve.
Figure 5:
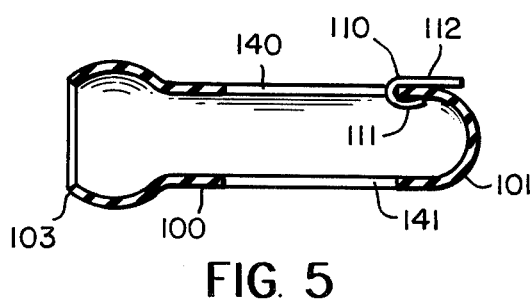
Figure 6:
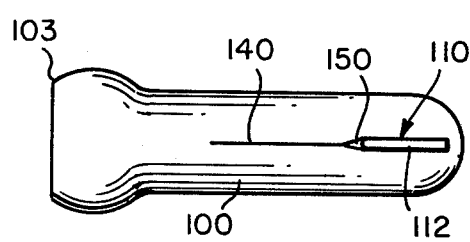

FIG. 4 shows the form of regulator valve I prefer over a variety of other forms. In this Figure, insofar as an element shown therein is the counterpart of an element shown in FIG. 1, it will be identified by the same reference numeral followed by zero. Comparing the two Figures, it will be evident that FIG. 4, over and above FIG. 1, includes elements 61 and 141. Element 61, however, is simply a third fitting which provides for having pump 3, comprising the flexible bulb 30, mounted directly on the casing 40, whereas element 141 is simply a second slit in nipple 100.

Some of the elements of FIG. 4 also differ from their counterparts in FIG. 1. Thus, the tube 10 counterpart is in form of a nipple 100 which, though closed at its end 101 and having a flanged open end 103, is generally circularly right cylindrical in form.

Again, the pin 10 is represented in FIGS. 4, 5, 6, 9 and 10 by the "d"-shaped member 110 preferably formed from a piece of 0.008 inch diameter, type 302 stainless steel wire having one end curved back on itself to form the loop 111 of the d, with the rest of the wire to its other end forming the leg 112 of the d, but leaving a space 113 a little narrower than the thickness of the wall of nipple 100, for receiving the wall, so as to securely fasten the d to the nipple in the end of slit 140 to form the variable opening 150, because the material of the tube in space 113 is gripped between leg 112 and loop 111.

In FIG. 4, it will be recognized that some means (not shown) will necessarily be provided to vent the outer end of bore 130 to the external atmosphere, since the regulator action requires a fixed back pressure less than the lowest value, to which it is desired to have the pressure bleed to in the cuff, for measuring purposes.

One reason for providing both slits 140 and 141 is to permit freer passage of air through the regulator valve 40, in response to squeezing the bulb 30. Likewise, by extending the pin through both slits, as shown in FIG. 11, an additional opening (not shown, but like opening 15, 16 and 150) results, which has the same properties, namely, the opening size increases as the cuff pressure decreases. In order to keep pin 21 in place, it is given U-form, wherein the U has relatively short legs 22 and 23, which by being duplicate, more or less make up for the lack of a space 113.

In another form, FIG. 12, the pin is provided in the form of the tang 32 of helical coil spring 31. The coils 33 of the spring frictionally fit the interior of tube 100. FIG. 13 provides an omega 41 having curved ends 42 and 43 in the slit 44 and its bright 45 in the nipple 100. The ends 42 and 43 hook over the nipple at the slit ends, thus both keeping the omega 41 in place and defining the variable openings 46 and 47.

Again, FIG. 14 provides the nipple 200, like nipple 100, but also having smaller nipple 102. A curved member 51 has a loop 52 at one end, secured around the nipple 102, and a hook 53 at the other end projecting into the end of slit 54 so as to define the variable opening 55. It will be noted that one obvious modification of this arrangement would be to install the member 51 with the hook 53 at the other end of the slit and the loop 52 at the other end of an ordinary nipple 100 since as shown in FIG. 4, this has a bulge at flared portion 120 around which the loop 52 could go, in order to secure both member 51 and the nipple in place.

Lastly, FIG. 15 shows a roughly C-shaped member 61, having one end 62 in the end of slit 64 to provide variable opening 65, and the other end lying against the outer surface of nipple 100 and immersed, in a bead of adhesive 66, whereby to secure the member 61 in place.

Starting with a top pressure of 300 mm. Hg gauge, my invention readily provides bleed giving pressure drop rates in the range of from 2 to 7 mm Hg per second, which are constant, for all instincts and purposes, to the lowest useful gauge pressure, in most cases, about 25 mm Hg, or less.

The foregoing description will enable one skilled in the art to practice my invention without difficulty. While the drawings are not manufacturing drawings, they are approximately to scale but much magnified, as will be evident when it is recalled that the various members in the valve slits were designed to be fabricated from a 0.2 inch long piece of 0.008 inch diameter wire, in the exact shape of FIGS. 9 and 10. In practice, the actual nipples will be about an inch long and be made of rubber of thickness to suit a gap 113 of 0.025 inch thickness or less.

I claim:

1. A sphygmomanometer system comprising fluid-containing means for applying a measured fluid pressure to a cardiovascular system for measuring pressures arising in said cardiovascular system, means for measuring pressures arising in said cardiovascular system, said sphygmomanometer system also including a regulator valve connected to said fluid-containing means for bleeding fluid from said fluid-containing means for decreasing said measured fluid pressure at a predetermined rate;

said regulator valve including a tube having a flexible wall, said tube being open at both ends, and having the opening at one said end formed with a slit having surfaces which sealingly contact each other when the pressure within said tube and the pressure without said tube are substantially the same;

said regulator valve also including a pin means in said tube for separating said surfaces somewhat, said pin means including a pin projecting into said slit, said tube being connected to said fluid-containing means, such as to expose the exterior of said tube to said measured fluid pressure, and its interior to a second fluid pressure lesser than said measured fluid pressure, whereby the said measured fluid pressure maintains said slit closed save for said pin.

2. The sphygmomanometer system of claim 1, wherein said one said end of said tube is flat with said slit being formed by flattened surfaces of the said wall of said tube.

3. The sphygmomanometer system of claim 1, wherein said one said end of said tube is in the form of a nipple having said slit therein.

4. The sphygmomanometer system of claim 3 wherein said nipple has a second slit therein.

5. The sphygmomanometer system of claim 4, wherein said pin passes through both slits.

6. The sphygmomanometer system of claim 5, wherein said second slit is opposite and parallel to the first said slit.

7. The sphygmomanometer system of claim 3, wherein said pin is the end of a coiled member having coils within, and effectively formed in the shape of, the interior of said nipple.

8. The sphygmomanometer system of claim 3, wherein said nipple has a lesser nipple thereon spaced from said slit, therebeing a wire coil about said lesser nipple, said coil providing said pin in the form of a curved end of said coil in said slit.

9. The sphygmomanometer system of claim 3, wherein said pin is provided in the form of an omega, the bight of which is within said tube and the legs of which project out of and curve over the ends of said slit.

10. The sphygmomanometer system of claim 3, wherein said pin is provided by a curved member secured at one end to the exterior surface of said tube, and having its other end in an end of said slit.

11. The sphygmomanometer system of claim 3, wherein said pin is provided by an elongated member having one end curved back on said member, said member grippingly receiving the wall of said tube between said one end and said member.

12. The sphygmomanometer system of claim 11 wherein said elongated member is in the form of a d, wherein the loop of the d is in the nipple and the leg of the d is outside the tube.

13. A regulator valve for bleeding fluid from fluid-containing means for decreasing fluid pressure therein at a predetermined rate:
    said regulator valve including a rubber tube, said tube being open at both ends, and having the opening at one said end formed with a slit having surfaces which sealingly contact each other when the pressure within said tube and the pressure without said tube are substantially the same;
    said regulator valve also including a pin means in said tube for separating said surfaces somewhat, said tube being adapted to be connected to said fluid-containing means such as to expose the exterior of said tube to said fluid pressure, and being adapted to have its interior connected to a second fluid pressure less than the first said fluid pressure, whereby said first said fluid pressure maintains said slit closed save for said pin;
    said pin means having a pin projecting into said slit but said pin means otherwise being totally contained within and supported on said one said end of said tube.

14. The regulator valve of claim 13 wherein said one said end of said tube is a nipple having a rounded closed end, said nipple having said slit in the side thereof.

15. The regulator valve of claim 14, wherein said nipple has a second slit therein said pin passes through both slits, and said pin has legs outside of said tube for retaining it in said slits.

16. The regulator valve of claim 15, wherein said second slit is opposite and parallel to the first said slit.

17. The regulator valve of claim 14, wherein said pin is the end of a coiled member having coils within, and effectively formed in the shape of, the interior of said nipple.

18. The regulator valve of claim 14, wherein said nipple has a lesser nipple thereon spaced from said slit, therebeing a wire coil about said lesser nipple, said coil providing a pin in the form of a curved end of said coil in said slit.

19. The regulator valve of claim 14, wherein said pin is provided in the form of an omega, the bight of which is within said tube and the legs of which project out of and curve over the ends of said slit.

20. The regulator valve of claim 14, wherein said pin is a curved member secured at one end to the exterior surface of said tube, and having its other end in an end of said slit.

21. The regulator valve of claim 14, wherein said pin is provided by an elongated member having one end curved back on said member, said member grippingly receiving the wall of said tube between said one said end and said member.

22. The regulator valve of claim 21, wherein said elongated member is in the form of a d, wherein the loop of the d is in the nipple and the leg of the d is outside the tube.

* * * * *